United States Patent
Choi et al.

(10) Patent No.: US 9,827,267 B2
(45) Date of Patent: Nov. 28, 2017

(54) MIXTURE OF SODIUM CHLORIDE AND SUGAR IN THE MANUFACTURE OF A MEDICAMENT EMPLOYED FOR TREATING LAX VAGINA SYNDROME OR COLPOXEROSIS DISEASE IN A MAMMAL

(71) Applicant: Won Seog Choi, Seoul (KR)

(72) Inventors: Won Seog Choi, Seoul (KR); Dong-Yeul Kwon, Daejeon (KR)

(73) Assignee: Won Seog Choi, Seoul (KR)

( * ) Notice: Subject to any disclaimer, the term of this patent is extended or adjusted under 35 U.S.C. 154(b) by 0 days.

(21) Appl. No.: 15/262,000

(22) Filed: Sep. 11, 2016

(65) Prior Publication Data

US 2016/0375053 A1    Dec. 29, 2016

Related U.S. Application Data

(63) Continuation of application No. 14/653,853, filed as application No. PCT/KR2014/008180 on Sep. 2, 2014, now abandoned.

(30) Foreign Application Priority Data

Oct. 1, 2013   (KR) ........................ 10-2013-0117300
May 2, 2014   (KR) ........................ 10-2014-0053161

(51) Int. Cl.
*A61K 33/14*      (2006.01)
*A61K 9/00*       (2006.01)
*A61K 31/7004*    (2006.01)

(52) U.S. Cl.
CPC ............ *A61K 33/14* (2013.01); *A61K 9/0034* (2013.01); *A61K 9/0036* (2013.01); *A61K 31/7004* (2013.01)

(58) Field of Classification Search
CPC ............ A61K 2300/00; A61K 31/7004; A61K 33/14; A61K 9/0034; A61K 9/0036
See application file for complete search history.

(56) References Cited

U.S. PATENT DOCUMENTS

2006/0105963 A1*  5/2006  Yang .................... A61K 9/0034
                                                   514/23
2008/0193428 A1*  8/2008  Zhou .................... A61K 31/192
                                                   514/1.1
2009/0232939 A1   9/2009  Berge
2012/0201904 A1*  8/2012  Choi .................... A61K 9/0034
                                                   424/680

FOREIGN PATENT DOCUMENTS

KR    10-2001-0029068 A    4/2001
KR    10-2011-0043448 A    4/2012
KR    10-1470282          12/2014
WO    WO 9743989 A1  *    11/1997
WO    2011-049327 A2      4/2011
WO    2012-072245 A2      6/2012
WO    2015-050324 A1      4/2015

OTHER PUBLICATIONS

S-J Oh, et al., (2003), Histological and functional aspects of different regions of the rabbit vagina, International Journal of Impotence Research, 15, pp. 142-150.
N. N. Kim et al., (2004), Effects of ovariectomy and steroid hormones on vaginal smooth muscle contractility, International Journal of Impotence Research, 16, pp. 43-50.
A. Giraldi et al., (2001), Joint Award Winning Paper D Jean Francois Ginestie Prize, Effects of diabetes on neurotransmission in rat vaginal smooth muscle, International Journal of Impotence Research, 13, pp. 58-66.
International Search Report, PCT/KR2014/008180, 4 pages.
Notice of Allowance, KR-10-0053161, dated Dec. 1, 2014 [Korean Original and English Translation].
Written Opinion, PCT/KR2014/008180, 7 pages.

* cited by examiner

*Primary Examiner* — Mark V Stevens
(74) *Attorney, Agent, or Firm* — Kirk Hahn

(57) ABSTRACT

The use of the mixture of a salt and sugar in the manufacture of a medicament employed for treating lax vagina syndrome or colpoxerosis disease in a mammal. Various tests, vaginal smooth muscle contractility test using New Zealand White Rabbit; (Experimental example 1); the effect on the vagina contractility in volunteers by using perinometer (Experimental example 2); and the effect on the colpoxerosis disease in volunteers (Experimental example 3), showed improving effect on the contractility of vagina tissue and colpoxerosis disease. Accordingly, the combination can be useful in treating or preventing lax vagina syndrome or colpoxerosis disease.

4 Claims, 3 Drawing Sheets

MIXTURE OF SODIUM CHLORIDE AND SUGAR IN THE MANUFACTURE OF A MEDICAMENT EMPLOYED FOR TREATING LAX VAGINA SYNDROME OR COLPOXEROSIS DISEASE IN A MAMMAL

This application is a Continuation of and claims priority upon U.S. application Ser. No. 14/653,853 filed on Jun. 19, 2015 (pending), which is a U.S. National Phase under 35 U.S.C. §371 of International Application PCT/KR2014/008180, filed on Sep. 2, 2014, which claims priority to Korean Patent Application No. 10-2014-0053161, filed on May 2, 2014 and Korean Patent Application No. 10-2013-0117300, filed on Oct. 1, 2013. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a use of the mixture of a salt and sugar in the manufacture of a medicament employed for treating lax vagina syndrome or colpoxerosis disease in a mammal.

Background Art

Lax vagina syndrome is designated as the vaginal syndrome characterized that the muscle located in vaginal cavity and vaginal opening area are loosened, the secretion of vaginal mucus is reduced and vaginal fascia is relaxed, and it frequently occurs after aging and childbirth, which may causes to the disadvantageous effect on rectum, uterus and bladder etc and it may exacerbate to occur serious problems, for example, fecal leakage, premature birth, stillbirth etc.

The representative phenomena of the disease are as follows: (1) the wind sound during sexual intercourse, (2) reduced frequency of orgasm feeling, (3) reduced sexual excitement caused by loosened vaginal muscle etc, which may be solved by various non-surgical therapy such as Kegel exercise well known as the pelvic muscle strengthening exercise to enforce pelvic muscle or surgical operation such as vaginal wall plastic operation for curing such worries but even if removing the loosened muscle with surgical operation, the muscle is not strengthened and have limited satisfaction.

The vaginal mucus of woman is increased during sexually exciting period as follows: the volume of blood flow is increased to vaginal tunic and thereby blood plasma is exuded from submucus capillary blood vessel. Colpoxerosis occurs by the reduced level of estrogen hormone before or after menopause and is characterized with the little secretion of vaginal fluid and reduced leukorrhea in spite of sexually excited period, which gives rise to various problems in conjugal sexual life, for example, vaginitis, vulvar or vaginal itching, dyspareunia, vaginismus postcoital spotting, dysuria, hematturia, severe pain caused by uterine contraction during or after orgasm, lower abdominal pain, the frequent occurrence of dysmenorrhea, vaginitidis, etc.

There have been still needed to develop effective therapies to treat lax vagina syndrome or colpoxerosis disease, effectively and safely till now.

Accordingly, there has been needed to develop novel therapeutic composition showing long-term treating activity with safety to treat lax vagina syndrome or colpoxerosis disease.

However, there has been not reported or disclosed on the therapeutic effect for lax vagina syndrome or colpoxerosis disease of the combination of salt and sugar in any of the above cited literatures, the disclosures of which are incorporated herein by reference.

To investigate an inhibitory effect of the combination of salt and sugar on lax vagina syndrome or colpoxerosis disease, the inventors of the present invention have carried out various experiments, for example, vaginal smooth muscle contractility test using by New Zealand White Rabbit; (Experimental example 1); the effect on the vagina contractility in volunteers by using perinometer (Experimental example 2); and the effect on the colpoxerosis disease in volunteers (Experimental example 3) and finally completed present invention by confirming that the combination showed improving effect on the contractility of vagina tissue and colpoxerosis disease in the test.

These and other objects of the present invention will become apparent from the detailed disclosure of the present invention provided hereinafter.

DISCLOSURE

Technical Problem

The present invention relates to a skin external composition comprising a salt and sugar as active ingredients for preventing and treating lax vagina syndrome or colpoxerosis disease and the use thereof.

The present invention relates to a use of the mixture of a salt and sugar in the manufacture of a medicament employed for treating lax vagina syndrome or colpoxerosis disease in a mammal.

Technical Solution

Accordingly, it is another object of the present invention to provide an external composition comprising a combination of salt and sugar as an active ingredient in an amount effective to treat or prevent lax vagina syndrome or colpoxerosis disease, together with a pharmaceutically acceptable carrier.

It is another object of the present invention to provide a use of a combination of salt and sugar in the manufacture of a medicament employed for treating or preventing lax vagina syndrome or colpoxerosis disease in a mammal.

It is the other object of the present invention to provide a method of treating or preventing lax vagina syndrome or colpoxerosis disease in a mammal wherein method comprises administering to said mammal an effective amount of a combination of salt and sugar, together with a pharmaceutically acceptable carrier thereof.

In one embodiment of the present invention, the present invention provides an external composition comprising a combination of salt and sugar as an active ingredient in an amount effective to treat or prevent lax vagina syndrome or colpoxerosis disease, together with a pharmaceutically acceptable carrier.

Additionally, the present invention provides a use of a combination of salt and sugar in the manufacture of a medicament employed for treating or preventing lax vagina syndrome or colpoxerosis disease in a mammal.

Additionally, the present invention provides a method of treating or preventing lax vagina syndrome or colpoxerosis disease in a mammal wherein method comprises administering to said mammal an effective amount of a combination of salt and sugar together with a pharmaceutically acceptable carrier thereof.

The term, "salt" defined herein comprise a processed salt such as melted salt or an un-refined salt such as sea salt, rock-salt etc, preferably, a refined salt such as sodium chloride or melted salt such as bamboo salt, more preferably, a melted salt prepared by melting a un-refined salt at the temperature ranging from 200 to 2000° C., preferably, from 800 to 1200° C., for the period ranging from 2 hours to 7 days, preferably, 12 hours to 48 hours.

The term, "sugar" defined herein comprise a saccharide compound, preferably, mono-saccharides such as glucose, fructose, mannose, galactose, etc or disaccharides such as lactose, maltose, sugar, etc, more preferably, glucose, more preferably, crystalline glucose.

The term, "a combination of salt and sugar" defined herein comprise a combination of salt and sugar mixed ratio of 1:1-30 (w/w), preferably, 1:1-10 (w/w), more preferably, 1:1-5 (w/w), most preferably, 1:1-3 (w/w).

The composition of the present invention may further contain the other antibiotics, dye, flavor etc in the amount of about 0.1~20% by weight of the above composition based on the total weight of the composition.

Hereinafter, the present invention is described in detail.

An inventive composition comprising the combination of salt and sugar can be prepared in detail by following procedures, For example, the inventive cleansing combination of the present invention can be prepared by follows; an un-refined salt such as sea salt, rock-salt etc is melted at the temperature ranging from 200 to 2000° C., preferably, from 800 to 1200° C., for the period ranging from 2 hours to 7 days, preferably, 12 hours to 48 hours to obtain the melted salt at the $1^{st}$ step; the melted salt is mixed with sugar compound, preferably, mono-saccharides such as glucose, fructose, mannose, galactose, etc or disaccharides such as lactose, maltose, sugar, etc, more preferably, glucose, more preferably, crystalline glucose with mixed ratio of 1:1-30 (w/w), preferably, 1:1-10 (w/w), more preferably, 1:1-5 (w/w), most preferably, 1:1-3 (w/w) to obtain inventive combination; and the combination is dissolved in an appropriate amount of distilled water, buffer, or isotonic solution, if necessary, with an appropriate amount of the other additives such as the other antibiotics, dye, flavor etc to obtain the inventive cleansing composition.

Accordingly, in an another embodiment of the present invention, the present invention provides a method for preparing the inventive cleansing combination comprising the step: of a processed salt such as melted salt or an un-refined salt such as sea salt, rock-salt etc at the temperature ranging from 200 to 2000° C., preferably, from 800 to 1200° C., for the period ranging from 2 hours to 7 days, preferably, 12 hours to 48 hours to obtain the melted salt at the $1^{st}$ step; mixing the melted salt with sugar compound, preferably, mono-saccharides such as glucose, fructose, mannose, galactose, etc or disaccharides such as lactose, maltose, sugar, etc, more preferably, glucose, more preferably, crystalline glucose with mixed ratio of 1:1-30 (w/w), preferably, 1:1-10 (w/w), more preferably, 1:1-5 (w/w), most preferably, 1:1-3 (w/w) to obtain inventive combination; and dissolving the combination in an appropriate amount of distilled water, buffer, or isotonic solution, if necessary, with an appropriate amount of the other additives such as the other antibiotics, dye, flavor etc to obtain the inventive cleansing composition.

It have been proved that the inventive composition comprising a combination of salt and sugar prepared by the above-described method showed potent improving effect on the contractility of vagina tissue and colpoxerosis disease through various experiments, for example, vaginal smooth muscle contractility test using by New Zealand White Rabbit; (Experimental example 1); the effect on the vagina contractility in volunteers by using perinometer (Experimental example 2); and the effect on the colpoxerosis disease in volunteers (Experimental example 3).

Accordingly, inventive skin external composition comprising a combination of salt and sugar prepared by the above-described method for treating or preventing lax vagina syndrome or colpoxerosis disease, together with a pharmaceutically acceptable carrier.

Additionally, the present invention provides a use of a combination of salt and sugar prepared by the above-described method in the manufacture of a medicament employed for treating or preventing lax vagina syndrome or colpoxerosis disease in a mammal.

Additionally, the present invention provides a method of treating or preventing lax vagina syndrome or colpoxerosis disease in a mammal wherein method comprises administering to said mammal an effective amount of a combination of salt and sugar prepared by the above-described method, together with a pharmaceutically acceptable carrier thereof.

The term "prevent" defined herein means the inhibition of such those diseases in a mammal which is prone to be caught by those disease and the term "treat" used herein means (a) the inhibition of the development of disease or illness; (b) the alleviation of disease or illness; or (c) the elimination of disease or illness.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as an inventive skin external composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the present invention may be formulated so as to provide quick, sustained or delayed release of the active ingredient after their administration to a patient by employing any of the procedures well known in the art.

For example, the compositions of the present invention can be dissolved in distilled water, pH buffer, oils, propylene glycol or other solvents that are commonly used in the art. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The inventive skin external composition of the present invention may be prepared in any form, for example, topical preparation such as cleansing liquid, gel, jelly, foam, cream, ointment, lotion, balm, patch, paste, spray solution, aerosol and the like, or insert preparation such as vaginal tablet, vaginal capsule, vaginal film, vaginal sponge, tampon, pad etc, preferably, vaginal tablet composition or cleansing liquid composition.

Accordingly, the present invention provides a cleansing liquid solution or vaginal tablet composition comprising a combination of salt and sugar for treating or preventing colpoxerosis, together with a pharmaceutically acceptable carrier.

The composition of the present invention in pharmaceutical dosage forms may be used in the form of their pharmaceutically acceptable salts, and also may be used alone or in appropriate association, as well as in combination with other pharmaceutically active compounds such as antibacterial compounds or extract derived from plant, animal or mineral well-known in the art.

The desirable dose of the inventive extract of the present invention varies depending on the condition and the weight of the subject, severity, drug form, route and period of administration, and may be chosen by those skilled in the art. However, in order to obtain desirable effects, it is generally recommended to administer at the amount ranging 0.001-1000 mg/kg, preferably, 0.01 to 100 mg/kg by weight/day of the combination of the present invention. The dose may be administered in single or divided into several times per day. In terms of composition, the inventive combination should be present between 0.01 to 99.99% by weight, preferably 0.1 to 99%, more preferably, 1 to 20%, most preferably, 5 to 10% by weight based on the total weight of the composition.

The composition of present invention can be administered to a subject animal such as mammals (rat, mouse, domestic animals or human) via various routes. All modes of administration are contemplated, for example, administration can be made externally, topically, orally, rectally or by intravenous, intramuscular, subcutaneous, intracutaneous, intrathecal, epidural or intracerebroventricular injection, preferably, externally or topically.

It will be apparent to those skilled in the art that various modifications and variations can be made in the compositions, use and preparations of the present invention without departing from the spirit or scope of the invention.

Advantageous Effects

As described in the present invention, through various tests, for example, vaginal smooth muscle contractility test using by New Zealand White Rabbit; (Experimental example 1); the effect on the vagina contractility in volunteers by using perinometer (Experimental example 2); and the effect on the colpoxerosis disease in volunteers (Experimental example 3), the inventive combination showed improving effect on the contractility of vagina tissue and colpoxerosis disease. Accordingly, the inventive combination can be useful in treating or preventing lax vagina syndrome or colpoxerosis disease.

BEST MODE

The above and other objects, features and other advantages of the present invention will more clearly understood from the following detailed description taken in conjunction with the accompanying drawings, in which;

BEST MODE FOR CARRYING OUT THE INVENTION

Figure 1:
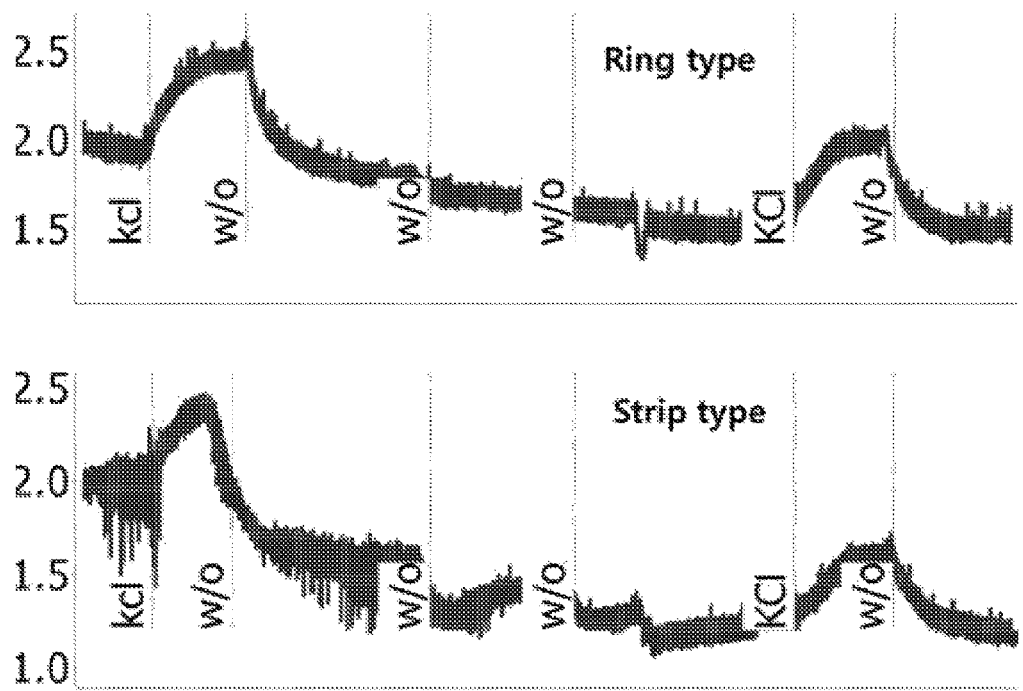
FIG. 1 shows the comparisons of each resting tension between ring type and strip type vaginal tissue.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1

Preparation of an Inventive Combination 1-1. Preparation of Processed Salt 900 mg of sea salt (Shinan, Korea, www.nhshinansalt-.com) was melted for 24 hours at 850-1000° C. using by heater (MS-E104, TOPS Co. Ltd.) to obtain 400 mg of the processed salt.

1-2. Preparation of Refined Salt 400 mg of refined salt (NaCl, F.W. 58.44) was procured from the conventionally available company (SPPO-91701, Duksan company, www.duksan.co.kr).

1-3. Preparation of Glucose 800 mg of glucose (crystalline glucose) was procured from the conventionally available company (Samyang Genex Corp., www.genex.co.kr).

1-4. Preparation of Combination (1)

400 mg of the processed salt and 800 mg of glucose prepared in the above steps, were thoroughly mixed together to obtain 1200 mg of the inventive combination (designated as "SG1" hereinafter).

1-5. Preparation of Combination (2)

400 mg of the refined salt and 800 mg of glucose prepared in the above steps, were thoroughly mixed together to obtain 1200 mg of the inventive combination (designated as "SG4" hereinafter).

The combinations were kept at −75° C. in refrigerator and used in following experiments by dissolving in distilled water before use.

Example 2

Preparation of Inventive Vaginal Tablet Composition (SG2)

The combination prepared in Example 1 comprising 400 mg of processed salt and 800 mg of glucose was mixed with 2 mg of magnesium stearate in order to formulating into inventive vaginal tablet composition combination (designated as "SG2" hereinafter) using by entableting apparatus (KT2000, Kumsungkigong).

Example 3

Preparation of Inventive Vaginal Tablet Composition (SG5)

The combination prepared in Example 1 comprising 400 mg of refined salt and 800 mg of glucose was mixed with 2 mg of magnesium stearate in order to formulating into inventive vaginal tablet composition combination (designated as "SG5" hereinafter) using by entableting apparatus (KT2000, Kumsungkigong).

Example 4

Preparation of Inventive Vaginal Cleansing Solution Composition

The vaginal cleansing solution composition comprising the combination prepared in Example 1 (SG4) comprising 400 mg of refined salt and 800 mg of glucose was prepared by mixing together with following ingredients as shown in Table 1 (designated as "SG3" hereinafter) for 48 hours with stirring.

TABLE 1

| SG3 solution (100 ml) | | |
| --- | --- | --- |
| | Ingredient | Amount |
| adjuvant | SG4 | 0.5 g |
| | Lactic acid | 1 g |
| | Whey | 180 mg |
| | Ethanol | 1 g |
| | Preservatives (benzalkonimum HCl and menthol) | Trace amount |
| Distilled water | Appropriate amount to adjusted to 100 ml | |

Experimental Example 1

Vaginal Smooth Muscle Contractility Test

To test the effect of inventive combination (SG3) prepared in Example on the vaginal smooth muscle contractility in New Zealand white rabbit, was performed by using organ bath according to the procedure disclosed in the literature (S-J Oh, et al., (2003), Histological and functional aspects of different regions of the rabbit vagina, *International Journal of impotence research*, 15, pp 142-150; N. N. Kim et al., (2004), Effects of ovariectomy and steroid hormones on vaginal smooth muscle contractility, *International Journal of Impotence Research*, 16, pp 43-50; A. Giraldi et al., (2001), Joint Award Winning Paper D Jean Francois Ginestie Prize Effects of diabetes on neurotransmission in rat vaginal smooth muscle, *International Journal of impotence Research*, 13, pp 58-66).

1-1. Preliminary Test

Prior to principal test, a preliminary test in order to determining the type of test was performed after delivering rabbit vagina in consideration with the previous literatures.

Through the preliminary test, it has been confirmed that the vaginal smooth muscle contractility in response to the addition of K+ (80 mM)-Krebs solution in the form of strip type rabbit vagina, showed stronger than that in the form of ring type rabbit vagina and moreover, the vaginal smooth muscle contractility according to the increased volume of phenylephrine in the form of strip type rabbit vagina, also showed stronger than that in the form of ring type rabbit vagina.

At the result, it has been confirmed that the strip type rabbit vagina is more suitable to test the experiment rather than ring type rabbit vagina.

1-2. Experimental Animal 10 rabbits (New Zealand White Rabbit, Saeron Bio Inc., Korea, about 2.5-3.0 kg, 1 week aged) had been acclimated with the environment for 3 days with checking their health condition and used in the experiment.

All the rabbits were marked with red oil-based pen during the acclimation period (to left ear auricle) and with black oil-based pen during test period (to right ear auricle). The breeding cages were marked with individual identification cards recording test number, test subject, test period and animal number etc.

The testing animal had been bred and test was performed in the animal breeding room of KAMSI (Korea Animal Medical Science Institute, Korea) under the condition maintaining the temperature (23±3° C.), relative humidity (55±15%), ventilation number (10-20 times/hr), light cycle (light on at 08:00 and light off at 20:00) and illumination intensity (150-300 Lux). The breeding condition was constantly and periodically checked. The animal had been freely accessible to feed (KSN140203, Cargill Adri Purina Inc., Korea) and sterilized water. The animals had been bred in stainless steel breeding box (W 405×L 605×H 365 mm) at 1 rabbit per cage during acclimation, quarantine, administration and observation period.

1-3. Sample Treatment (Organ Bath Method)

The inventive composition was administrated into the rabbit vaginal tissue according to the organ bath method disclosed in the literature as follows:

The strip (1.5 mm×10 mm) of rabbit vagina surrounded with muscle of which mucose membrane had been removed, was dipped into Krebs solution (119 mM NaCl, 4.7 mM KCl, 1.1 mM $MgSO_4$, 1.2 mM $KH_2PO_4$, 1.5 mM $CaCl_2$, 25 mM $NaHCO_3$, 10 mM D-glucose, G1009, Biosesang Corp. Korea) saturated with mixture gas (95% $O_2$ and 5% $CO_2$ gas) at 37° C. The end of trip was fixed and the other end was connected to transducer (model FT03; Grass instruments, Quincy, Mass., USA) to record the isometric tension of the strip with grass physiograph (AD instruments, USA) in 20 mL of chamber (FT03, GRASS Technologies).

1-4. Procedure

Through various preliminary test with different conditions, following procedure was established. After stabilizing the strip of rabbit vagina with resting tension of 1.2 g for 30-60 mins in Krebs solution, the strip was contracted twice for 15 mins in K+ Krebs solution (43.7 mM NaCl, 80 mM KCl, 11 mM $MgSO_4$, 1.2 mM $KH_2PO_4$, 1.5 mM $CaCl_2$, 18 mM $NaHCO_3$, 10 mM D-glucose, Biosesang Corp. Korea), washed with the solution three times to be stabilized and the comparative test for determining its contractility was performed.

The intensity of vagina contractility was determined by comparing the contractility caused by K+ Krebs solution per tissue weight and the intensity of vagina contractility in a dose dependent manner was expressed by setting each intensity of K+ contractility to 100%.

1-5. Determination of Resting Tension

Two kinds of rabbit vagina, i.e., ring type (3 mm) and strip type (1.5 mm×10 mm) were prepared and the resting tension of the vagina was chosen where the vagina was most stable and the contractility response against the addition of K+ Krebs solution after the stabilization had shown most apparently.

As can be seen in FIG. 1 and Table 2, the contractility of ring type was 0.51 g in K+ Krebs solution when its resting tension was set to 2.0 g whereas it was increased to 0.54 g when its resting tension was set to 1.5 g. Accordingly, the testing tension of ring type was determined to 1.5 g considering the above test result and the stability of vagina tissue.

The contractility of strip type was 0.31 g in K+ Krebs solution and severe convulsion happened when its resting tension was set to 2.0 g whereas it was increased to 0.42 g when its resting tension was set to 1.2 g. Accordingly, the testing tension of strip type was determined to 1.2 g considering the above test result and the stability of vagina tissue.

TABLE 2

Resting tension in ring type and strip type vagina tissue

|  | Ring type (tension unit: g) | strip type (tension unit: g) |
| --- | --- | --- |
| Resting tension | 1.97 | 2.12 |
| K+ Krebs | 2.48 | 2.43 |
| Tension difference | 0.51 | 0.31 |
| Resting tension | 1.52 | 1.24 |
| K+ Krebs | 2.06 | 1.66 |
| Tension difference | 0.54 | 0.42 |

1-6. Test Result

Figure 2:
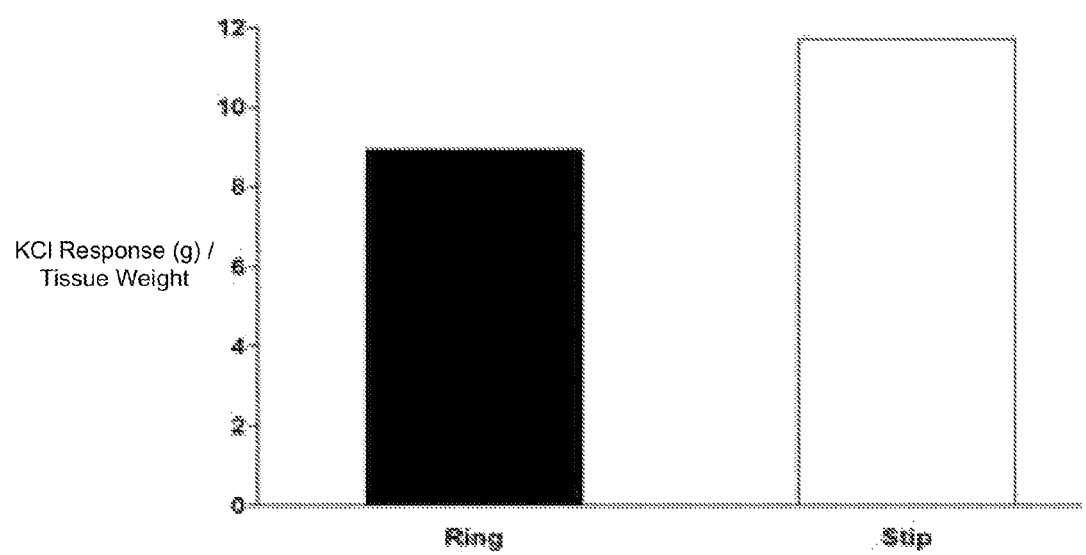
FIG. 2 shows the intensity of contractility in response to the addition of K+ Krebs in ring type and strip type vaginal tissue.

At the result, it has been confirmed that the strip type vagina tissue was chosen to use in the experiment since it showed the stronger contractility response against K+ (80 mM)-Krebs than the strip type vagina tissue (See FIG. 2).

Figure 3:
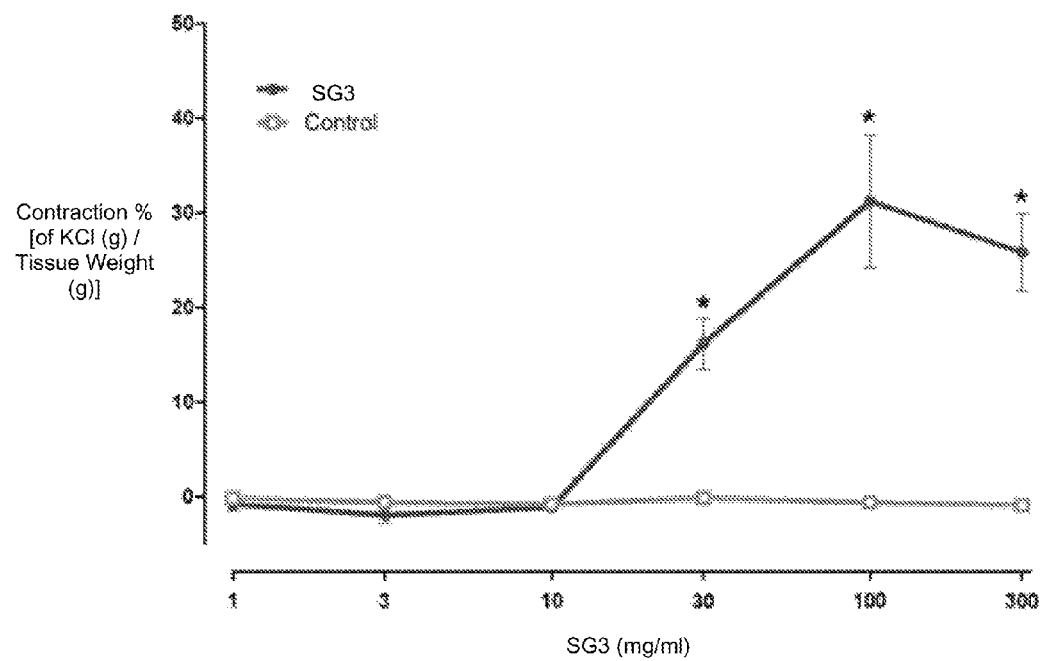
FIG. 3 shows the intensity of contractility according to the dose of test samples.

It has been confirmed that the contractility intensity in the test group treated with inventive composition (30-300 mg/ml) has been increased in a dose dependent manner compared with control group which was not treated with test sample (*p<0.05 vs. control, See FIG. 3)

Accordingly, it has been confirmed that the invention composition showed potent improving effect on the contractility of vagina tissue at 30-300 mg/ml (P<0.001).

TABLE 3

Contractility according to increased dose of test sample

| dose (mg/ml) | sample | N | Mean | SEM |
| --- | --- | --- | --- | --- |
| 1 | SG3 | 10 | −0.815 | 0.716 |
|  | control | 6 | −0.178 | 0.398 |
| 3 | SG3 | 10 | −1.947 | 0.940 |
|  | control | 6 | −0.622 | 0.428 |
| 10 | SG3 | 10 | −1.153 | 0.425 |
|  | control | 6 | −0.813 | 0.451 |
| 30 | SG3 | 10 | 16.173 | 2.708 |
|  | control | 6 | −0.140 | 0.441 |
| 100 | SG3 | 10 | 31.226 | 7.015 |
|  | control | 6 | −0.647 | 0.360 |
| 300 | SG3 | 10 | 25.836 | 4.125 |
|  | control | 6 | −0.898 | 0.374 |

Experimental Example 1

Brief Clinical Test (1)

The vaginal tablet composition (SG2) prepared in Example was administrated intra-vaginally once a day for 5 days to 100 volunteers consisting of 35 patients suffering from lax vagina syndrome, and 65 normal women ranging from 20 to 50 years who live in Korea and the effect on the vagina contractility of inventive composition was surveyed and determined by using perinometer (peritro9300, Laborie Medical Technologies Canada ULC).

The perinometer (peritro9300, Laborie Medical Technologies Canada ULC) for determining a vaginal pressure has a different size varied with a different pressure, i.e., at 0 cm $H_2O$: length 8 cm and diameter 26 mm; at 100 cm $H_2O$, length 8 cm and diameter 30.5 mm. The apparatus surrounded with condom was inserted into the volunteer's vagina to the extent that the tip of apparatus had reached to 7 cm depth of vagina. The volunteer' body was to be relaxed by spreading her legs and relaxing vaginal muscle. After turning on the apparatus, the measures have zeroed in on precisely and probe was inflated by inserting air to the extent that the value had reached to 100 cm $H_2O$. The measures have zeroed again in on precisely and the vagina of volunteer being cautious with not moving waist or pelvis, has been forced to be strongly constricted and lasted for 5 seconds to determine the contractility of vagina muscle. The volunteers were allowed to have a rest for at least 1 min after repetitive determination and the mean value of the contractility was calculated by determining three times for 1 volunteer.

At the result, it has been confirmed that the internal pressure of vaginal muscle treated with inventive composition was remarkedly increased to about 38% (after 3 days) and about 52% (after 5 days) as can be seen in Table 4.

TABLE 4 result of vaginal contractility (unit: $cmH_2O$)

|  | Before treatment | 3 days after the treatment | 5 days after the treatment |
| --- | --- | --- | --- |
| Mean | 42.72 | 58.96 | 64.98 |
| standard deviation | ±12.58 | ±13.25 | ±13.91 |

Experimental Example 2

Brief Clinical Test (2)

The vaginal insertion tablet composition (SG5) prepared in Example was administrated externally twice a day for 3 days to 100 volunteers consisting of 35 patients suffering from colpoxerosis disease, and 65 normal women ranging from 20 to 50 years who live in Korea and the effect on the vaginal dryness (A) before and (B) after the treatment with inventive composition was determined. The survey result was categorized into 5 grades according the vaginal dryness after the treatment, i.e., (1) the amount of leukorrhea was much reduced, (2) the amount of leukorrhea was little reduced, (3) the amount of leukorrhea was not changed, (4) the amount of leukorrhea was little increased, (2) the amount of leukorrhea was much increased.

At the result, it has been confirmed that the amount of leukorrhea was increased in more than 83% volunteers after the treatment of inventive composition.

Accordingly, it has been confirmed that the inventive composition is useful in treating colpoxerosis disease, as can be seen in Table 5.

TABLE 5

| test result on colpoxerosis disease | | | | | |
|---|---|---|---|---|---|
| grade | (1) | (2) | (3) | (4) | (5) |
| Number of volunteers | 3 | 4 | 10 | 64 | 19 |

Accordingly, it has been proved that the inventive composition can be useful in treating lax vagina syndrome or colpoxerosis disease.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The present invention relates to a use of the mixture of a salt and sugar in the manufacture of a medicament employed for treating lax vagina syndrome or colpoxerosis disease in a mammal. As described in the present invention, through various tests, for example, vaginal smooth muscle contractility test using by New Zealand White Rabbit; (Experimental example 1); the effect on the vagina contractility in volunteers by using perinometer (Experimental example 2); and the effect on the colpoxerosis disease in volunteers (Experimental example 3), the inventive combination showed improving effect on the contractility of vagina tissue and colpoxerosis disease. Accordingly, the inventive combination can be useful in treating or preventing lax vagina syndrome or colpoxerosis disease.

The invention claimed is:

1. A method of treating lax vagina syndrome or colpoxerosis disease in a mammal, comprising the steps of:
   administering into a vagina of a mammal in need of treatment for lax vagina syndrome or colpoxerosis disease an effective amount of a combination consisting of:
   salt, comprising sodium chloride, selected from the group consisting of refined salt and un-refined salt, and
   a mono-saccharide selected from the group consisting of glucose, fructose, mannose, and galactose;
   together with a pharmaceutically acceptable carrier thereof,
   wherein the sodium chloride and the mono-saccharide comprise 20% to 99.99% by weight of the composition and wherein the weight ratio of the sodium chloride and the mono-saccharide is 1:1 to 1:10.

2. The method of claim 1, wherein the combination is contained in a composition selected from the group consisting of cleansing liquid, gel, jelly, foam, cream, ointment, lotion, balm, patch, paste, spray solution, aerosol, vaginal tablet, vaginal capsule, vaginal film, vaginal sponge, tampon, and pad.

3. The method of claim 2, wherein the composition is a cleansing liquid.

4. The method of claim 2, wherein the composition is a vaginal tablet.

* * * * *